(12) United States Patent
Siess et al.

(10) Patent No.: US 12,029,891 B2
(45) Date of Patent: *Jul. 9, 2024

(54) VENTRICULAR ASSIST DEVICE CONTROL

(71) Applicant: Abiomed Europe GmbH, Aachen (DE)

(72) Inventors: Thorsten Siess, Aachen (DE); Walid Aboulhosn, Aachen (DE); Christoph Nix, Aachen (DE); Katrin Lunze, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,252

(22) Filed: Feb. 18, 2022

(65) Prior Publication Data

US 2022/0241578 A1 Aug. 4, 2022

Related U.S. Application Data

(63) Continuation of application No. 16/342,924, filed as application No. PCT/EP2017/076295 on Oct. 16, 2017, now Pat. No. 11,285,311.

(30) Foreign Application Priority Data

Oct. 19, 2016 (EP) .................................... 16194558

(51) Int. Cl.
*A61M 1/10* (2006.01)
*A61M 60/13* (2021.01)
(Continued)

(52) U.S. Cl.
CPC ............ *A61M 60/50* (2021.01); *A61M 60/13* (2021.01); *A61M 60/135* (2021.01);
(Continued)

(58) Field of Classification Search
CPC ........ A61M 2205/3334; A61M 60/531; A61M 2205/3365; A61M 2205/50;
(Continued)

(56) References Cited

U.S. PATENT DOCUMENTS

| 5,911,685 A | 6/1999 | Siess et al. |
| 11,285,311 B2 * | 3/2022 | Siess .................... A61M 60/135 |

(Continued)

FOREIGN PATENT DOCUMENTS

| CN | 1909829 A | 2/2007 |
| CN | 101518661 A | 9/2009 |

(Continued)

OTHER PUBLICATIONS

Office Action for corresponding Chinese Patent Application No. 201780064836.X dated Apr. 1, 2022 (17 pages).

(Continued)

*Primary Examiner* — Jon Eric C Morales
(74) *Attorney, Agent, or Firm* — Botos Churchill IP Law LLP

(57) ABSTRACT

A control device for a ventricular assist device (VAD) with settable speed levels. The control device includes an input configured to receive at least one measuring signal related to a physiological condition of the circulatory system of a patient receiving heart assistance by the VAD, where the control device is configured to derive an actual value of at least one characteristic parameter of the heart from one or more of the at least one measuring signal and to provide a refined actual value of the at least one characteristic parameter in which effects of physiologically caused fluctuations are eliminated or reduced. The control device further includes an output configured to output an updated setting value for the speed level, where the control device is
(Continued)

configured to produce the updated setting value based on the refined actual value and a predeterminable set-point value.

20 Claims, 7 Drawing Sheets

(51) Int. Cl.
| | |
|---|---|
| *A61M 60/135* | (2021.01) |
| *A61M 60/139* | (2021.01) |
| *A61M 60/216* | (2021.01) |
| *A61M 60/295* | (2021.01) |
| *A61M 60/416* | (2021.01) |
| *A61M 60/422* | (2021.01) |
| *A61M 60/50* | (2021.01) |
| *A61M 60/515* | (2021.01) |
| *A61M 60/531* | (2021.01) |
| *A61M 60/538* | (2021.01) |
| *A61M 60/546* | (2021.01) |

(52) U.S. Cl.
CPC ........ *A61M 60/139* (2021.01); *A61M 60/216* (2021.01); *A61M 60/295* (2021.01); *A61M 60/416* (2021.01); *A61M 60/422* (2021.01); *A61M 60/515* (2021.01); *A61M 60/531* (2021.01); *A61M 60/538* (2021.01); *A61M 60/546* (2021.01); *A61M 2205/3334* (2013.01); *A61M 2205/3365* (2013.01); *A61M 2205/50* (2013.01); *A61M 2230/06* (2013.01); *A61M 2230/30* (2013.01); *A61M 2230/42* (2013.01)

(58) Field of Classification Search
CPC .......... A61M 2230/04; A61M 2230/30; A61M 60/13; A61M 60/135; A61M 60/148; A61M 60/178; A61M 60/216; A61M 60/422; A61M 60/50; A61M 60/538; A61M 60/546; A61M 60/857; A61M 2205/33; A61M 2205/3303; A61M 2205/3317; A61M 2205/3344; A61M 2205/3523; A61M 2230/06; A61M 2230/42; A61M 60/139; A61M 60/205; A61M 60/221; A61M 60/237; A61M 60/295; A61M 60/414; A61M 60/416; A61M 60/515; A61M 60/523; A61M 60/562; A61M 60/569; A61M 60/816; A61M 60/873; A61B 5/0215; A61B 5/0538; A61B 5/6869
See application file for complete search history.

(56) References Cited

U.S. PATENT DOCUMENTS

| | | | |
|---|---|---|---|
| 2003/0045772 | A1 | 3/2003 | Reich et al. |
| 2005/0107658 | A1 | 5/2005 | Brockway |
| 2015/0073203 | A1 | 3/2015 | Wariar et al. |
| 2015/0306290 | A1* | 10/2015 | Rosenberg ........... A61B 5/0538 600/16 |
| 2019/0209755 | A1* | 7/2019 | Nix ..................... A61M 60/205 |

FOREIGN PATENT DOCUMENTS

| | | |
|---|---|---|
| CN | 102686150 A | 9/2012 |
| CN | 103747815 A | 4/2014 |
| JP | H0330774 A | 2/1991 |
| WO | 03015609 A2 | 2/2003 |
| WO | 2005051838 A2 | 6/2005 |
| WO | 2005077265 A1 | 8/2005 |
| WO | 2014085806 A1 | 6/2014 |

OTHER PUBLICATIONS

International Search Report and Written Opinion for Application No. PCT/EP2017/076295 dated Jan. 15, 2018.
Office Action for corresponding Chinese Patent Application No. 201780064836.X dated Jun. 3, 2021 (21 pages).
Office Action from corresponding Japanese Patent Application No. 2022-139624 dated Nov. 28, 2023 (6 pp.).

* cited by examiner

VENTRICULAR ASSIST DEVICE CONTROL

CROSS-REFERENCE TO RELATED APPLICATIONS

This application claims priority under 35 U.S.C. § 120 and is a continuation of U.S. application Ser. No. 16/342,924, filed on Apr. 17, 2019, issued as U.S. Pat. No. 11,285,311, which is a national phase entry under 35 U.S.C. § 371 of International Application No. PCT/EP2017/076295, filed on Oct. 16, 2017, published in English, which claims priority from European Application No. 16194558.9, filed on Oct. 19, 2016, the disclosures of each of which are hereby incorporated herein by reference.

FIELD OF THE INVENTION

The present invention concerns the field of ventricular assist devices. In particular, the invention relates to a control device for controlling a ventricular assist device (VAD), such as an intravascular rotary blood pump, and the VAD comprising the control device for controlling the VAD.

BACKGROUND OF THE INVENTION

If the pumping function of a patient's heart is insufficient despite optimal medical treatment, the circulatory system can be assisted by a VAD. VADs may assist or even substitute the insufficient ventricular pumping function of a heart by delivering blood parallel to the ventricle of the heart. To this end, a VAD typically is configured to take blood from the blood circulation at an inlet to eject it back to the blood circulation at an outlet. In doing so, the VAD needs to overcome the pressure difference between the outlet and the inlet, i.e. between afterload and preload of the VAD.

One exemplary embodiment of a VAD is a catheter-based rotary blood pump that is arranged to be placed or implanted directly into the heart for several hours or days for assisting the heart function until recovery. For example, U.S. Pat. No. 5,911,685 A discloses a non-pulsatile intravascular rotary blood pump. However, there are other types of VADs as well. The intravascular rotary blood pump known from U.S. Pat. No. 5,911,685 A comprises two pressure sensors for respectively measuring the surrounding blood pressure at their respective location once the blood pump is implanted in a heart.

For example, at intensive care units, patients with insufficient heart function assisted by a VAD may be ventilated, i.e. receive assistance in breathing. Breathing assistance is provided by external ventilation resulting in a rhythmic inflation and deflation of the patient's lung. This external ventilation causes a corresponding change in intrathoracic pressure, as well. The change in intrathoracic pressure results in a corresponding fluctuation in the cardiovascular and/or intracardiac heart pressures. Particularly, during inspiration (inflation) the intrathoracic pressure is higher than during expiration (deflation).

At normal or coronary care ward, a conscious patient receiving heart assistance may breathe autonomously. Then, the aforementioned effects occur in an inverted way, i.e. during inspiration the intrathoracic pressure is lower than during expiration.

In the afore-discussed exemplary contexts, it was found that the described pressure changes result in fluctuations in measured vascular and/or intracardiac pressures. As a possible consequence, these fluctuations may affect the stability of blood pump speed control. Moreover, the detection or avoidance of events such as suction may be disturbed. It is noted these are just two particular examples of how fluctuations in monitored vascular and/or intracardiac measurement signals may influence the control of a VAD. Moreover, the assisted or autonomous breathing described a possible cause is just an example, as well. Other examples of physiologically caused fluctuations may be pressure fluctuations caused by an intra-aortic balloon pump therapy, an external counter-pulsation therapy, by a change of positioning of the patient's body, for example, into the Trendelenburg position.

BRIEF SUMMARY OF THE INVENTION

There is the need for an improved control device for a VAD, such as an intravascular blood pump, and a corresponding VAD comprising the control device, which are improved with regard to effects of physiologically caused fluctuations in one or more measuring signals taken from a patient receiving heart assistance by the VAD on the control of the VAD, in particular on the control of the speed of the VAD, which speed is related to the blood flow produced by the VAD, such as a rotational speed of a rotational intravascular blood pump. Further, it is desired to provide a method for obtaining a refined actual value of at least one characteristic parameter of the heart, in which effects of physiologically caused fluctuations in the one or more measuring signals from which the actual value is derived are eliminated or at least reduced. Further, there is need for a method for controlling the speed level of a VAD based on the refined actual value.

The object is achieved by the features of the independent claims. Advantageous embodiments and further developments are defined in the respective dependent claims.

The basic idea of the herein-proposed improvement is the elimination or at least reduction of physiologically caused fluctuations in an actual derived value of at least one characteristic parameter of the heart, which can be used in the control of the VAD speed, e.g. the rotational pump speed of an intravascular blood pump. In particular, instabilities, such as oscillations, of the controlled VAD speed controlled by a close-loop control can be avoided or at least reduced. For example, as a characteristic parameter of the heart of a patient receiving heart assistance by the VAD, the end-diastolic left ventricular pressure may be used. Based on this, the VAD speed may be adjusted automatically by means of a closed-loop control so that the monitored end-diastolic left ventricular pressure achieves a desired setpoint value; also other characteristic parameters may be used in the control of the VAD speed. It was found that there are physiologically caused fluctuations in the measurement signal(s) which blur the "true" actual value of a characteristic parameter derived there-from. This, for example, may cause instabilities in controlled VAD speed. For example, a monitored end-diastolic left ventricular pressure as one characteristic parameter may be affected by autonomous or assisted breathing of the patient so that the control of the VAD speed is affected as well. Eliminating or at least reducing these physiologically caused fluctuations makes the controlled VAD speed more stable. Thus, it is proposed to make the "true" actual value of the at least one characteristic parameter of the heart available.

For sake of clarity, the following definitions will be used herein:

The term "characteristic parameter of the heart" is to be understood as a particular value derived from a physiological signal that is able to characterize a heart's condition with respect to, for example, loading, such as overloaded or unloaded, and/or a physiological condition, such as weak, strong, or recovered.

The "circulatory system" is an organ system that permits blood to circulate. The essential components of the human circulatory system are the heart, blood and blood vessels. The circulatory system includes the pulmonary circulation, a "loop" through the lungs where blood is oxygenated; and the systemic circulation, a "loop" through the rest of the body to provide oxygenated blood.

A first aspect relates to a control device for a ventricular assist device (VAD) that comprises settable speed levels, and particular embodiments and further developments thereof discussed herein below. The "settable speed levels" may be discrete speed levels, e.g. certain discrete rotational velocities of a rotational blood pump, or continuously settable speed levels in a range that is defined by a minimum speed and a maximum speed. The speed level is associated with the blood flow produced by the VAD and thus, the provided assistance to the heart. However, there is not necessarily a direct relation between the VAD speed and the produced blood flow since the pressure difference between inlet and outlet of the VAD is affecting the blood flow produced at a particular VAD speed, too.

The control device comprises at least one input configured to receive at least one measuring signal. The at least one measuring signal represents or contains information on at least one physiological value (which may be called also quantity) which is related to the circulatory system of a patient receiving heart assistance by the VAD.

The control device is configured to derive an actual value of at least one characteristic parameter of the heart from the at least one measuring signal; i.e. the at least one characteristic parameter may be derived from two or more measuring signals as well.

The control device is further configured to provide a refined actual value of the at least one characteristic parameter in which physiologically caused fluctuations are eliminated or reduced. The refined actual value is in accordance to the discussion above the "true" actual value which is not blurred by the physiologically caused fluctuations on the one or more measuring signals on which the at least one characteristic parameter is based.

The control device further comprises an output configured to output an updated setting value for the speed level of the VAD.

Preferably, the control device is configured to produce the updated setting value based on the current refined actual value of the at least one characteristic parameter and a predeterminable set-point value therefor. For example, to this end, the control device may implement a closed-loop control by which the at least one characteristic parameter is controlled by means of adjusting the speed level of the VAD so that the monitored at least one characteristic parameter achieves the predetermined sept-point value.

Preferably, the control device is configured to process the at least one measuring signal and/or actual value of the at least one characteristic parameter to provide the refined actual value of the at least one characteristic parameter.

To this end, the control device may be configured to process a plurality of actual values of the characteristic parameter within a moving time interval. The time interval preferably includes the current actual value of the characteristic parameter and further historical values, i.e. the time interval starts in the past and ends at the point in time of the current actual value of the characteristic parameter. Preferably, the time interval is settable by a user of the control device or adjustable by the control device.

A plurality of actual values of the at least one characteristic parameter may be stored as a time series of the actual values of the characteristic parameter. The time series may comprise a limited number of actual values of the at least one characteristic parameter. Preferably, the limited number of actual values of the characteristic parameter may correspond to values which belong to a current moving time interval that includes the current actual value of the characteristic parameter and further historical or past values within the current time interval. The time interval ends at the current actual value and goes back into the past by a predefined time frame. The further historical values within the time interval may comprise all actual values of the at least one characteristic parameter located within the time interval. However, the time series may also just comprise every other, every third, or every fifth and so on of the values of the characteristic parameter within the time interval. Thus, the time series comprises a row of consecutive actual values or a sequence of actual values.

In a particular embodiment, the current refined actual value of the characteristic parameter is a moving average value of the current actual value of the characteristic parameter and further historical or past values within the moving time interval. Additionally or alternatively, the current refined actual value of the characteristic parameter may be based on a moving average value of the at least one measuring signal from which the characteristic parameter is derived.

In a particular application, the physiologically caused fluctuations in the characteristic parameter may be caused by pressure fluctuations in the thorax of the patient. The pressure fluctuations may be due to assisted or autonomous breathing of the patient. More particular, the fluctuations may be correlated with the breathing frequency or the ventilation frequency, when the patient is receiving breathing assistance by ventilation of the lung. Other reasons may cause the fluctuations as well. For example, the physiologically caused fluctuations may be pressure fluctuations caused by an Intra-Aortic Balloon Pump (IABP), by an external counter-pulsation (ECP) therapy, by a change of the position of the body of the patient, for example changing the body into the Trendelenburg position, just to name some more examples.

For short, an IABP is a mechanical device that increases myocardial oxygen perfusion while at the same time increasing cardiac output. The IABP may consist of a cylindrical balloon positioned in the aorta, the inflation and deflation of which is controlled to counter-pulsate with respect to the pulsation of the heart. ECP is a procedure performed on patients by means of pneumatic cuffs on the legs, the cuffs are timed to inflate and deflate based on the patient's electrocardiogram, ideally inflating at the beginning of diastole and deflating at the beginning of systole. ECP is similar to the IABP, since it increases pressure in the aorta while the heart is relaxing during diastole. In the Trendelenburg position, the body is laid flat on the back with the feet higher than the head by 15-30 degrees, in contrast to the reverse Trendelenburg position, where the body is tilted in the opposite direction.

To this end, the control device may be configured to determine a frequency correlated with the physiologically caused fluctuations to be eliminated or at least reduced, e.g. the breathing or ventilation frequency, based on the at least one measuring signal and/or historical actual values of the characteristic parameter. For example, the breathing or ventilation frequency may be detected by measuring the time between the occurrences of minimum or maximum values in the measurement signal. For example, the ventilation frequency VF (or correspondingly the breathing frequency, as well) may be calculated by the time interval between two consecutive maxima (or minima) of the at least one measuring signal or the at least one characteristic parameter.

For example, in case the measuring signal is the left-ventricular pressure LVP and the characteristic parameter is defined as the end-diastolic left-ventricular pressure EDLVP. Thus, the actual breathing frequency VF may be determined as $$VF = (t_{k,EDLVP,max} - t_{k-1,EDLVP,max})^{-1}, \text{ and/or}$$

$$VF = (t_{k,LVP,max} - t_{k-1,EDLVP,max})^{-1},$$

at point in time $t_{k-1}$ of an occurrence of the used reference value, e.g. the left-ventricular pressure LVP or the end-diastolic left-ventricular pressure EDLVP and point in time $t_k$ of the re-occurrence.

To eliminate or reduce the physiologically caused fluctuations, the control device may be configured to process the one or more of the at least one measuring signal and/or a sequence of actual values of the at least one characteristic parameter by applying a moving average filter. The moving average filter may have a size that is related to a periodicity of the physiologically caused fluctuations to be eliminated. Alternatively or additionally, the control device may be configured to process the one or more of the at least one measuring signal and/or the sequence of actual values of the at least one characteristic parameter by applying a high-pass filter having a characterizing cut-off frequency related to the physiologically caused fluctuations to be eliminated.

For example, in the exemplary application in which the physiologically caused fluctuations are related to breathing, the periodicity of the fluctuations is correlated with the breathing frequency or ventilation frequency. Thus, the moving average filter may have a size related to the breathing frequency or ventilation frequency. That is to say, the size of the moving average filter may define the time interval.

As the at least one measuring signal, at least one pressure in the circulatory system of the patient may be used. For example, the at least one measuring signal may be at least one of the left ventricular pressure LVP, the aortic pressure AoP, the central venous pressure CVP, the pulmonary artery pressure PAP, and an ECG signal of the patient, just to name some preferred examples.

As the at least one characteristic parameter, a particular value of a vascular and/or intracardiac blood pressure at a predetermined event of the cardiac cycle may be used.

In further developments, the at least one characteristic parameter may be derived from at least two particular values of a vascular and/or intracardiac blood pressure at a predetermined event of the cardiac cycle. For example, the at least one characteristic parameter may by a pressure gradient between two intracardiac pressures at two particular events during one cardiac cycle.

For example, the at least one characteristic parameter may be the filling gradient $$FG\left( = \frac{\Delta LVP}{\Delta t}\bigg|_{FG} \right)$$

of the left ventricular pressure LVP during the diastolic phase of the cardiac cycle which is here defined between point in time tow of the opening of the mitral valve and consecutive the point in time $t_{CMV}$ of the closing of the mitral valve as $$FG = \frac{\Delta LVP}{\Delta t}\bigg|_{FG} = \frac{LVP(t_{CMV,j+1}) - LVP(t_{OMV,j})}{t_{CMV,j+1} - t_{OMV,j}},$$

wherein j depicts a particular cardiac cycle, i.e. j+1 indicates the cardiac cycle following the cardiac cycle j, with j=1, 2, 3, . . . .

Based on the filling gradient FG as the at least one characteristic parameter, the control device may be configured to produce updated setting values so that the filling gradient becomes or is kept positive and close to zero. Most preferably, the control device is configured to keep the filling gradient zero.

Alternatively or additionally, the at least one characteristic parameter may be the diastolic relaxation or systolic contraction of the heart.

The systolic contraction is defined as the positive quotient of the difference of the left ventricular pressure value observed at the moment of closing of the mitral valve and at the moment of opening of the aortic valve divided by the time span there-between, i.e. the time spend from closing of the mitral valve until opening of the aortic valve.

The diastolic relaxation is defined as the quotient of the difference of the left ventricular pressure value observed at the moment of closing of the aortic valve and at the moment of opening of the mitral valve divided by the time span therebetween, i.e. the time spend from closing of the aortic valve and opening of the mitral valve.

Additionally, the control device may be further configured to calculate an actual heart rate based on the time interval between an occurrence and a consecutive recurrence of one of the at least one characteristic parameter.

Additionally or alternatively, the control device may be configured to calculate an actual blood flow produced by the VAD as one particular characteristic parameter.

Regarding the update of the setting value, the control device may be configured to produce an updated setting value each time there is predetermined deviation of the at least one refined actual value of the at least one characteristic parameter from the corresponding predeterminable set-point value. Additionally or alternatively, the control device may be configured to update the setting value when a new refined actual value of the characteristic parameter has been produced. Additionally or alternatively, the control device may be configured to update the setting value periodically, i.e. with a predetermined update frequency.

A second aspect relates to a VAD for assistance of a heart of patient.

The VAD comprises, i.e. is connected or coupled to, any one of the control device as described in accordance with the first aspect above.

In a particular and exemplary preferred embodiment, the VAD is a non-pulsatile rotational blood pump. The blood pump is preferably a catheter-based blood pump. Most preferably, the VAD is a low inertia device by featuring one or more of the following characteristics (a) to (c): (a) moving, in particular rotating, parts, for example a rotor or impeller, of the VAD comprise low masses by being made of a low-weight material, for example plastic; (b) a driving means, such as an electric motor, is arranged near, preferably very near, most preferably adjacent, to a part, for example a rotor or impeller, driven by the motor, and, if catheter-based, preferably having no rotational drive cable; (c) a coupling or connection, for example a shaft, of the motor with a part, for example a rotor or impeller, driven by the motor is short; all moving, in particular rotating, parts of the VAD have small diameters.

For example, the control device for a VAD as described in accordance with the first aspect may be particularly useful in connection with a catheter-based rotary blood pump, the blood flow through which can be controlled directly based on the at least one determined characteristic parameter. Such a blood pump is known, for example, from U.S. Pat. No. 5,911,685 A. In this context, the control device is a so-called pump controller for controlling the rotational speed, i.e. the speed levels of the blood pump.

Basically, such a blood pump is arranged for a temporary placement or implantation into the left or right heart. For left-sided heart assistance, the blood pump is arranged to be positioned inside the left ventricle of the heart of a patient via the aorta such that finally the blood pump protrudes with a cannula through the aortic valve opening to enable blood to be pumped across the aortic valve from the left ventricle into the aorta by means of a pumping device through the cannula.

For an alternative right-sided heart assistance, the blood pump is arranged to be positioned in the vena cava before the right heart such that the blood pump protrudes with its cannula through the tricuspidal valve opening bridging the right atrium and the right ventricle for pumping a blood flow from the vena cava directly into the pulmonary artery by means of the pumping device through the cannula.

For example, the pumping device may comprise a motor section and a pump section fastened to the distal end of the motor section; but other configurations are possible as well, e.g. in which the motor is distal to an outlet of the pump section. The pump section may further comprise a tubular pump housing with a thrust element, such as an impeller, rotating therein. The thrust element may be seated on a motor shaft protruding out of the motor section. Alternatively, other ways of coupling the motor with the drive are possible such as a magnetic coupling of a rotating sealed motor with a thrust element, such as an impeller. Extending from the distal end of the pump section may be the flow cannula adapted such that in operation of the blood pump, blood can be sucked through by the pumping device, or can be ejected when the pumping pump flow direction is reversed.

As it regards the configuration of the control device, the control device may implement a data acquisition unit with at least one input for receiving external and internal signals. For example, one input may be configured to receive the at least one measuring signal, which may be for example a vascular or intracardiac pressure signal.

The at least one measuring signal may be gathered internally, for example, by one or more sensors which may be integrated into or onto the VAD or may be sensors implantable to the patient. Alternatively or additionally, the at least one measuring signal may be gathered externally, for example, by means of additional monitoring systems.

It is noted, "external" means here a signal external to the system comprising the control device and the VAD. In turn, "internal" means a signal that is already present in the control device and/or the VAD or that is provided by a component of the control device and/or the VAD.

Further, the control device may comprise or be connected or coupled to a user inter-face with input and output means. For example, an input means may be one or more input devices such as keys and/or buttons to be pressed and/or rotational buttons to be rotated and so on. The output means may be a display device for displaying information such as setting information for the control device, operational data of the control device and/or the VAD and so on. In particular, the input means and output means may be integrated in part or completely in one entity such as a touch screen device. Input signals from the input devices may be forwarded to the data acquisition unit for further use, e.g. as setting data for the control device.

For example, the user interface may be, among other things, configured so that a user can select a particular parameter among the at least one characteristic parameter to be used in the control of the speed level of the VAD. Furthermore, the user interface may provide a corresponding input means configured so that the user can define a corresponding set-point value for the at least characteristic parameter, which may be selectable by the user as needed; i.e. the set-point value is predeterminable by a user. Alternatively or additionally, an input for a set-point value may be provided by other internal units of the control device itself. Such other internal units may be configured for signal processing and/or analyzing, such as the herein below discussed data processing unit. Alternatively or additionally, set-point values may be provided by an expert system unit, as well.

The control device has the output configured to output the updated setting value. Here it is noted, "output" does not necessarily mean that a signal is to be output by the control device to another external entity. An "output" may also be a certain point inside the control device, for example, an output of an internally implemented unit of the control device which unit is configured to perform a particular function or functionality.

As said above, in the context of the exemplary catheter-based rotary blood pump as one exemplary embodiment of the VAD, the setting value for the speed level of the VAD may be a setting value for the rotational speed of the pumping device of the blood pump. For example, the setting value for the rotational speed may correspond to a rotational speed to be established by the rotating thrust element driven by the electrical motor of the pumping device.

As it regards the acquisition of the measurement signals, for example, at least two pressure sensors may be arranged on or integrated into the VAD so that one sensor detects the pressure at the inlet, i.e. the preload, of the VAD and the other sensor detects the pressure at the outlet, i.e. the afterload, of the VAD. Alternatively or additionally, the VAD may comprise a pressure sensor by which the pressure difference between the preload and the afterload can be detected.

The at least one pressure sensor may be implemented by any suitably pressure sensor. Preferably, the one or more pressure sensors are read out, i.e. sampled or pulled with a frequency of at least about 250 Hz.

For example, when the VAD is arranged for left-sided heart assistance, the VAD may comprise a first pressure sensor at the inlet to be located in the left ventricle when the VAD is positioned in the left heart. The pressure sensor can be used in generating a measuring signal representing the left ventricular pressure as at least one physical value. An additional and alternative blood pressure representing a physical value related to the circulatory system may be the aortic pressure AoP. Accordingly, the VAD may comprise additionally or alternatively a pressure sensor at the outlet to be located in the aorta when the blood pump is positioned in the left heart. For left-sided heart assistance, preferably the at least one characteristic parameter may be at least one of:

an aortic pressure value observable at the moment of closing of the aortic valve, an aortic pressure value observable at the moment of opening of the aortic valve, an end-diastolic left ventricular pressure observable at the moment of closing of the mitral valve, and a left ventricular pressure observable at the moment of opening of the mitral valve. Further possible characteristic parameters may be the above discussed pressure gradients, such as the filling gradient, the diastolic relaxation, and the systolic contraction of the heart.

Correspondingly, in the case that the VAD is arranged for right-sided heart assistance, the inlet of the VAD may be located in the vena cava or right ventricle and the outlet may be located in the pulmonary artery, thus the physical quantity related to the circulatory system may be the central venous pressure CVP and/or the pulmonary arterial pressure PAP. Characteristic parameters may be derived correspondingly as discussed above in connection with the left-sided heart support.

It is worth to be noted that also other devices may serve as a source providing a useful measuring signal that represents a physical value related to the circulatory system. For example, such sensor may comprise electrodes of an electrocardiogram (ECG) device that are, for example, attachable to the skin of the patient. Such an ECG signal provided by the ECG device may be used as one measuring signal representing one physical value related to the circulatory system.

The control device may comprise at least one computing unit for implementing internal units which are configured for internal functions or functionalities of the control device. The computing unit may comprise hardware and software in any combination thereof. That is to say, the computing unit may comprise programmable hardware that can be configured by means of corresponding computer programs comprising software code for causing the programmable hardware to perform, for example, the respective required steps of a particular function or functionality of the control device as described herein. Programmable computing units are in general well known in the art and to the person skilled in the art and therefore need no detailed description.

Of course, a computing unit may comprise particular dedicated hardware which comprises hard-coded particular functions, such as field-programmable gate arrays (FPGAs) and/or one or more dedicated processors such as a signal processor for processing and/or analyzing e.g. the at least one measuring signal. In this regard, the control device may be structurally comprised of hardware units and/or software modules both implementing respective functional units which cooperate in controlling the speed of the VAD. For simplicity, it is assumed that the herein described functions and functionalities are considered as all together being implemented by the control device. It is noted, particular functions of the control device are described herein with reference to dedicated units implemented in or by the control device and configured for particular functions or functionalities but in general the association of particular functions or functionalities with particular units can be adapted as needed.

Firstly, the control device may implement the above-mentioned data acquisition unit. The data acquisition unit may be configured to collect externally and internally measured signals. Secondly, the control device may implement a signal processing unit. The signal processing unit may be configured to derive the characteristic parameter by processing the at least measurement signals. For example, the signal processing unit may be configured to determine the end diastolic left ventricular pressure as at least one characteristic parameter from a measuring signal representing the left ventricular pressure over time. Alternatively or additionally, the signal processing unit may be further configured to produce further values usable as characteristic parameter, based on the at least one derived characteristic parameter and/or the at least one measuring signal. Thirdly, the control device may implement a signal analysis unit. The signal analysis unit may be configured to analyze external and internal signals and/or the at least one characteristic parameter over time. For example, the signal analysis unit may be configured to, for example, predict the next occurrence of particular events in the cardiac cycle of the assisted heart. For example, such an event may be the point in time, a next occurrence of the closing of the aortic valve is expected. Moreover, the signal analysis unit may be configured to perform the above-discussed processing of the at least one measuring signal and/or the actual values of the at least one characteristic parameter to provide the refined actual values thereof. Fourthly, the control device may implement a speed command unit. In general, the speed command unit may be configured to provide a speed command signal indicating the speed level to be established by the VAD, e.g. by a motor of the VAD, such as the electrical motor of the exemplary rotational blood pump. Sixthly, the control device may implement a motor control unit; but the motor control unit may be external to the control device, too. The motor control unit may be configured to adjust the speed level of the VAD in accordance with the current speed command signal to establish a speed in accordance to the current actual setting value for the speed. For example, in the context of the rotary blood pump, the motor control unit may be configured to adjust the rotational blood pump speed by changing the electrical power supplied to the electrical motor of the blood pump. For example, the motor control unit may adjust an electrical motor current supplied to the motor of the blood pump. Finally, the signal processing unit and the signal analyzing unit may be implemented by one unit such as a data processing unit.

As discussed above, the signal processing and/or signal analyzing unit may be configured to determine the at least one characteristic parameter, based on a derivative of the corresponding measuring signal.

For example, the characteristic parameter may be the end-diastolic left ventricular pressure. To this end, the control device may be configured to use a measuring signal $LVP_{meas}$ of the left ventricular pressure LVP as an intracardiac pressure and the derivative thereof. Further, the at least one characteristic parameter may be the end-diastolic left ventricular pressure EDLVP which may be detected by sampling or pulling based on the first and/or second derivative of the measuring signal representing the left ventricular pressure. To this end, the actual value of the EDLVP may be derived based on the measuring signal $LVP_{meas}$ and/or a derivative d/dt of the measuring signal $LVP_{meas}$. Also additional signals may be used as well.

For example, an actual value of the EDLVP may be detected based on the first derivative of the measuring signal $LVP_{meas}$. The measuring signal $LVP_{meas}$ may be differentiated with respect to time, i.e. $dLVP_{meas}/dt$. When the first derivative $dLVP_{meas}/dt$ reaches or exceeds a predetermined threshold $v_{threshold}$, and/or when other suitable conditions are valid, then at that this particular point in time $t_k$ the actual $EDLVP(t_k)$ value can be determined.

For example, the predetermined threshold $v_{threshold}$ may be set individually for a particular patient, e.g. by means of an ECG. For example, the control device may be configured to compare the measuring signal $LVP_{meas}$ with an ECG signal or a trigger signal based thereon. For instance the EDLVP may be detected shortly after occurrence of the R-wave in the corresponding ECG signal. The threshold $V_{threshold}$ may be adjusted accordingly such that it matches the first derivative $dLVP_{meas}/dt$ at the time of or shortly after the appearance of the R-wave in the ECG signal. That is to say, the particular value for the first derivative $dLVP_{meas}/dt$ can be set by reference to another signal, which may be, for example, the ECG signal.

Alternatively, an actual value of EDLVP may also be determined by means of the employment of the ECG signal only. For example, the control device may be configured to monitor the ECG signal with respect to the R-wave which approximately coincides with the occurrence of the EDLVP. Alternatively, the control device may just receive and use a trigger signal indicating the occurrence of the R-wave to determine the actual value of the LVP as the current actual value of the EDLVP.

The calculation of an actual blood flow produced by the VAD may be as follows, for example, in the context of the rotary blood pump as an exemplary VAD, the control device may be configured to calculate the actual blood flow through the blood pump based on an actual pressure difference between the inlet and the outlet of the blood pump, the actual speed of the blood pump, and the electrical power supplied to the blood pump. Preferably, to this end, the control device may have access to a stored set of characteristic curves representing the relationship between these parameters. The set of characteristic curves may be stored in a memory of the computing unit or a memory in the blood pump accessible by the computing unit. For example, the set of characteristic curves may be stored in form of a look-up table.

BRIEF DESCRIPTION OF THE DRAWINGS

Hereinafter the invention will be explained by way of examples with reference to the accompanying drawings; in which

Now with reference to FIGS. 1 and 2, FIG. 1 shows a catheter-based rotational blood pump (in the following called "blood pump") on the left-hand side, which is described herein as one exemplary embodiment of a VAD, while the exemplary blood pump is shown in more detail in FIG. 2.

Figure 1:
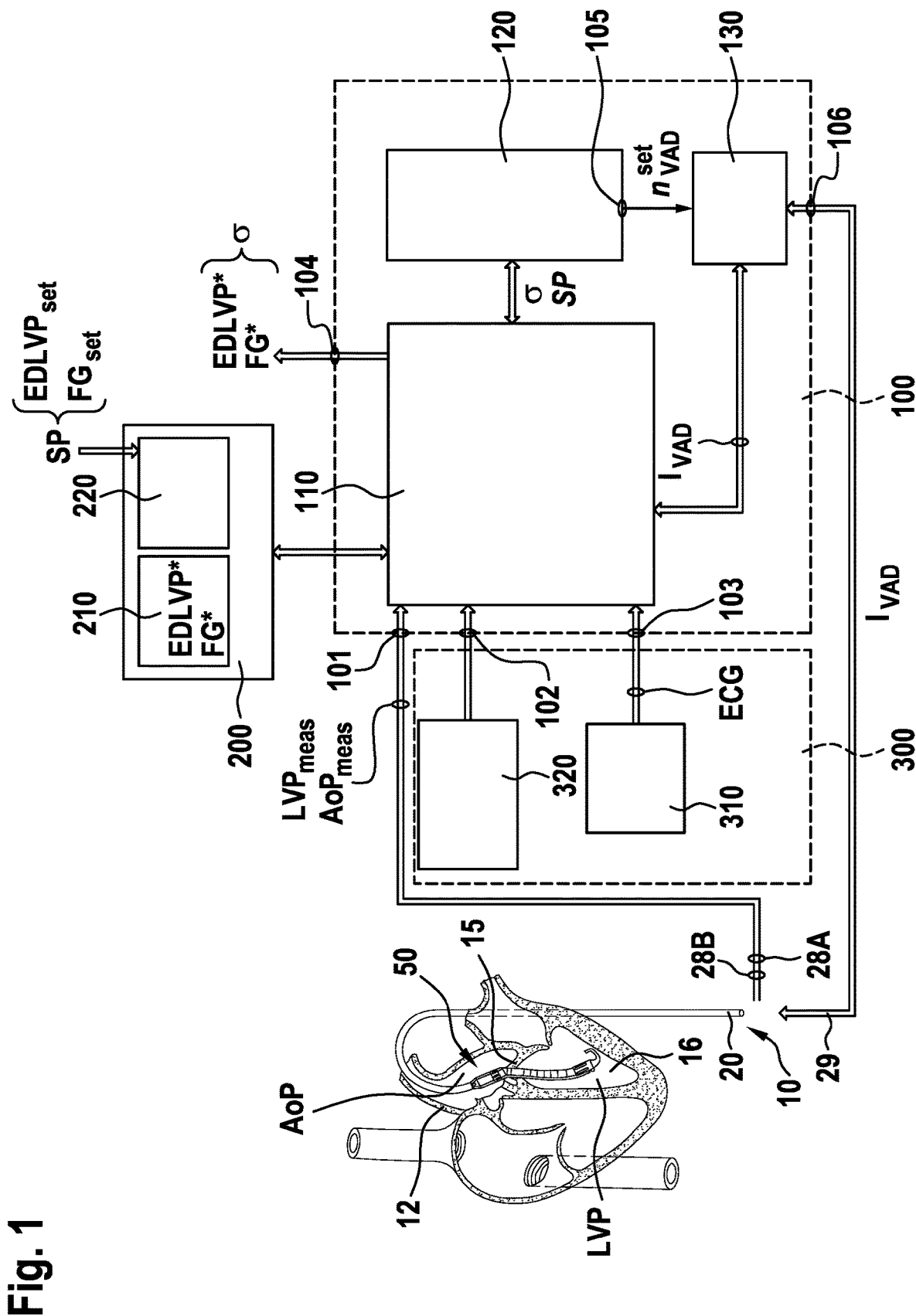
FIG. 1 shows a catheter-based intravascular blood pump as an example of a VAD which is placed through the aorta and extending through the aortic valve into the left ventricle of a heart, and a simplified block diagram of an embodiment of a control device for the blood pump.

The blood pump is based on a catheter 10, by means of which the blood pump is temporarily introduced through the aorta 12 and the aortic valve 15 into the left ventricle 16 of a heart. As shown in more detail in FIG. 2, the blood pump comprises in addition to the catheter 10 a rotary pumping device 50 fastened to the end of a catheter tube 20. The rotary pumping device 50 comprises a motor section 51 and a pump section 52 located at an axial distance therefrom. A flow cannula 53 is connected to the pump section 52 at its one end, extends from the pump section 52 and has an inflow cage 54 located at its other end. The inflow cage 54 has attached thereto a soft and flexible tip 55. The pump section 52 comprises a pump housing having outlet openings 56. Further, the pumping device 50 comprises a drive shaft 57 protruding from the motor section 51 into the pump housing of the pump section 52. The drive shaft 57 drives an impeller 58 as a thrust element by means of which, during operation of the rotary pumping device, blood can be sucked through the inflow cage 54 and discharged through the outlet openings 56.

The pumping device 50 can also pump in the reverse direction when adapted accordingly, e.g. as required when the blood pump is placed in the right heart. In this regard and for the sake of completeness, FIG. 1 shows the rotary blood pump as one particular example of a VAD located in and for assistance of the left heart. For assistance of the right heart, the rotary blood pump of the present example may be introduced into the right heart from the vena cava and located in the right heart so that blood can be ejected into the pulmonary artery. In this configuration, the blood pump may be configured for sucking in blood from the vena cava or from the right ventricle and for ejecting the blood into the pulmonary artery. That is to say, the principles and functionalities described by the one particular embodiment may be transferred correspondingly for right-sided heart assistance. Thus, no detailed description is required.

Figure 2:
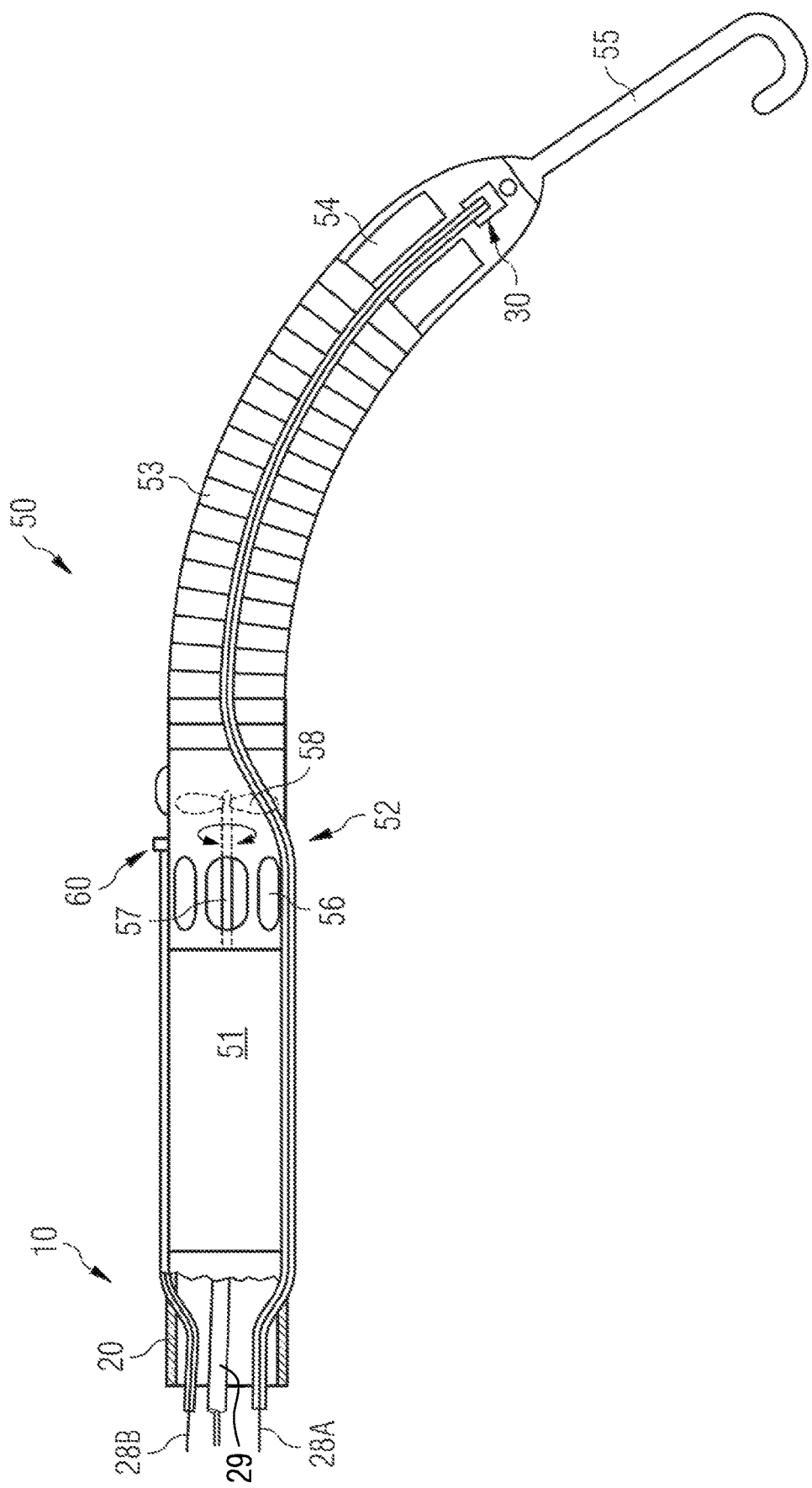
FIG. 2 shows a side view of the VAD of FIG. 1 with some details.

In FIGS. 1 and 2, three lines, two signal lines 28A and 28B and a power-supply line 29 for suppling an electrical current to the motor section 51, pass through the catheter tube 20 of the catheter 10 to the pumping device 50. The two signal lines 28A, 28B and the power-supply line 29 are attached at their proximal end to a control device 100. It goes without saying that there may be additional lines for further functions; for example, a line for a purge fluid (not shown) may pass through the catheter tube 20 of the catheter 10 to the pumping device 50 as well. Additional lines may be added based on different sensing technologies.

As shown in FIG. 2, the signal lines 28A, 28B are parts of blood pressure sensors with corresponding sensor heads 30 and 60, respectively, which are located externally on the housing of the pump section 52. The sensor head 60 of the first pressure sensor is associated with signal line 28B. The signal line 28A is associated with and connected to the sensor head 30 of the second blood pressure sensor. The blood pressure sensors may, for example, be optical pressure sensors functioning according to the Fabry-Perot principle as described in U.S. Pat. No. 5,911,685 A, wherein the two signal lines 28A, 28B are optical fibers. However, other pressure sensors may be used instead. Basically, signals of the pressure sensors, which carry the respective information on the pressure at the location of the sensor and which may be of any suitable physical origin, e.g. of optical, hydraulic or electrical etc. origin, are transmitted via the respective signal lines 28A, 28B to corresponding inputs of a data processing unit 110 of the control device 100. In the example shown in FIG. 1, the pressure sensors are arranged so that the aortic pressure AoP is measured by sensor head 60 and the left ventricular pressure LVP is measured by sensor head 30.

The data processing unit 110 is connected via an input 101 with the respective signal lines 28A, 28B to receive the corresponding measuring signals $AoP_{meas}$ for the aortic pressure AoP and $LVP_{meas}$ the left ventricular pressure LVP.

The data processing unit 110 is configured for acquiring external and internal signals, for signal processing, such as calculation of a difference between two pressure signals as a basis for estimating pump flow, for signal analysis, such as deriving an actual value of an at least one characteristic parameter σ, such as the end-diastolic left ventricular pressure EDLVP or a filling gradient FG of the heart which is to be forwarded to a speed command signal generator 120.

The data processing unit 110 is connected via corresponding signal lines at inputs 102, 103 to additional measurement devices 300, e.g. an electrocardiograph (ECG) 310. The ECG 310 provides an ECG signal to the data processing unit 110. The device 310 is exemplary and not limiting, i.e. other external measuring devices represented by device 320 may supply useful signals and may be used as well.

The control device 100 further comprises a user interface 200 comprising a display 210 as an output means and an input device 220 as input means such as a keyboard, buttons etc. The display device 210 and the input device 220 are integrated partly together in form of a touch screen device. On the display 210, setting parameters, monitored parameters, such as measured pressure signals, and other information, such as setting menus etc., can be displayed. Particularly, refined actual values, such as the EDLVP* or FG*, of the at least one characteristic parameter σ may be displayed via the display device 210 to a user. Further, by means of the user interface 220, the user of the control device 100 and the VAD can interact with the control device 100, e.g. by changing desired settings of the system.

Further, the refined actual values, such as the EDLVP*, FG*, of the at least one characteristic parameter σ, in which effects of physiologically caused fluctuations are eliminated or reduced, are provided at output 104 for external use as needed.

The data processing unit 110 is also configured to provide the refined actual value, such as e.g. EDLVP* or FG*, of the at least on characteristic parameter σ. The refined actual value of the at least on characteristic parameter σ is forwarded to a speed command signal generator 120.

The speed command signal generator 120 is configured to generate and adjust, i.e. update, an actual speed command signal $n_{VAD}^{set}$ and to supply it to a speed control unit 130. The speed command signal $n_{VAD}^{set}$ is provided by the command signal generator 120 operating in an outer feedback loop in which the command signal generator 120 is continuously fed with the refined actual value of the at least on characteristic parameter σ.

The command signal generator 120 also receives a corresponding set-point value SP, such as $EDLVP_{set}$ or $FG_{set}$, for the at least one characteristic parameter σ. The set-point value SP is also provided by the data processing unit 110. The command signal generator 120 is configured to generate based on an error signal ERR (cf. FIG. 3) corresponding to an actual difference between the refined actual value, such as the EDLVP* or FG*, of the at least on characteristic parameter σ and the corresponding set-point value SP the actual speed command signal $n_{VAD}^{set}$ For example, the actual speed command signal $n_{VAD}^{set}$ may be generated based on the error signal in the manner of proportional-integral-derivative (PID) controller 125 (cf. FIG. 3), or any other alternative controller such as a fuzzy controller. The generated actual speed command signal $n_{VAD}^{set}$ is forwarded to the speed control unit 130.

Accordingly, the speed control unit 130 controls the speed $n_{VAD}$ of the VAD, in accordance with the received speed command signal $n_{VAD}^{set}$. With reference the rotational blood pump as an exemplary VAD, the speed control unit 130 supplies a motor current $I_{VAD}$ to the motor section 51 of the pumping device 50 via the power-supply line 29 that leads through the catheter tube 20. The actual level of the supplied motor current $I_{VAD}$ corresponds to the electrical current required by the pumping device 50 to establish the target speed level defined by the actual speed command signal $n_{VAD}^{set}$ Via the power-supply line 29, the pumping device 50 may communicate with the control unit 100, i.e. may provide a signal corresponding to the actual rotational speed.

A measuring signal of the supplied motor current $I_{VAD}$ is an example of an internal signal to the control device 100 which is also provided to the data processing unit 110 for further processing and use.

According to the first aspect the control device 100 for pumping device 50 as an embodiment of a VAD with settable speed levels comprises the input 101 that is configured to receive the measuring signal $LVP_{meas}$ of the left ventricular pressure LVP that represents a physical value related to the circulatory system of the patient receiving heart assistance by the VAD.

The control device 100 is configured to provide a refined actual value EDLVP* or FG* of at least one characteristic parameter in which physiologically caused fluctuations are eliminated or at least reduced. To this end, in the embodiment shown, the data processing unit 110 is configured to derive an actual value of the EDLVP as an actual value of at least one characteristic parameter σ of the heart from the measuring signal $LVP_{meas}$.

The data processing unit 110 is further configured to process the measuring signal $LVP_{meas}$ or the actual value EDLVP or FG in order to provide the refined actual value EDLVP* or FG* in which the physiologically caused fluctuations are eliminated. An output of the data processing unit 110 forwards the refined actual value EDLVP* or FG* of the at least one characteristic parameter σ to the speed command unit 120.

The speed command unit 120, in turn, provides at output 105 a correspondingly updated speed command signal $n_{VAD}^{set}$ as the current setting value to the motor control unit 130.

The motor control unit 130 supplies a corresponding motor current $I_{VAD}$ required by the pumping device 50 to establish the target speed level as defined by the speed command signal $n_{VAD}^{set}$.

Figure 3:
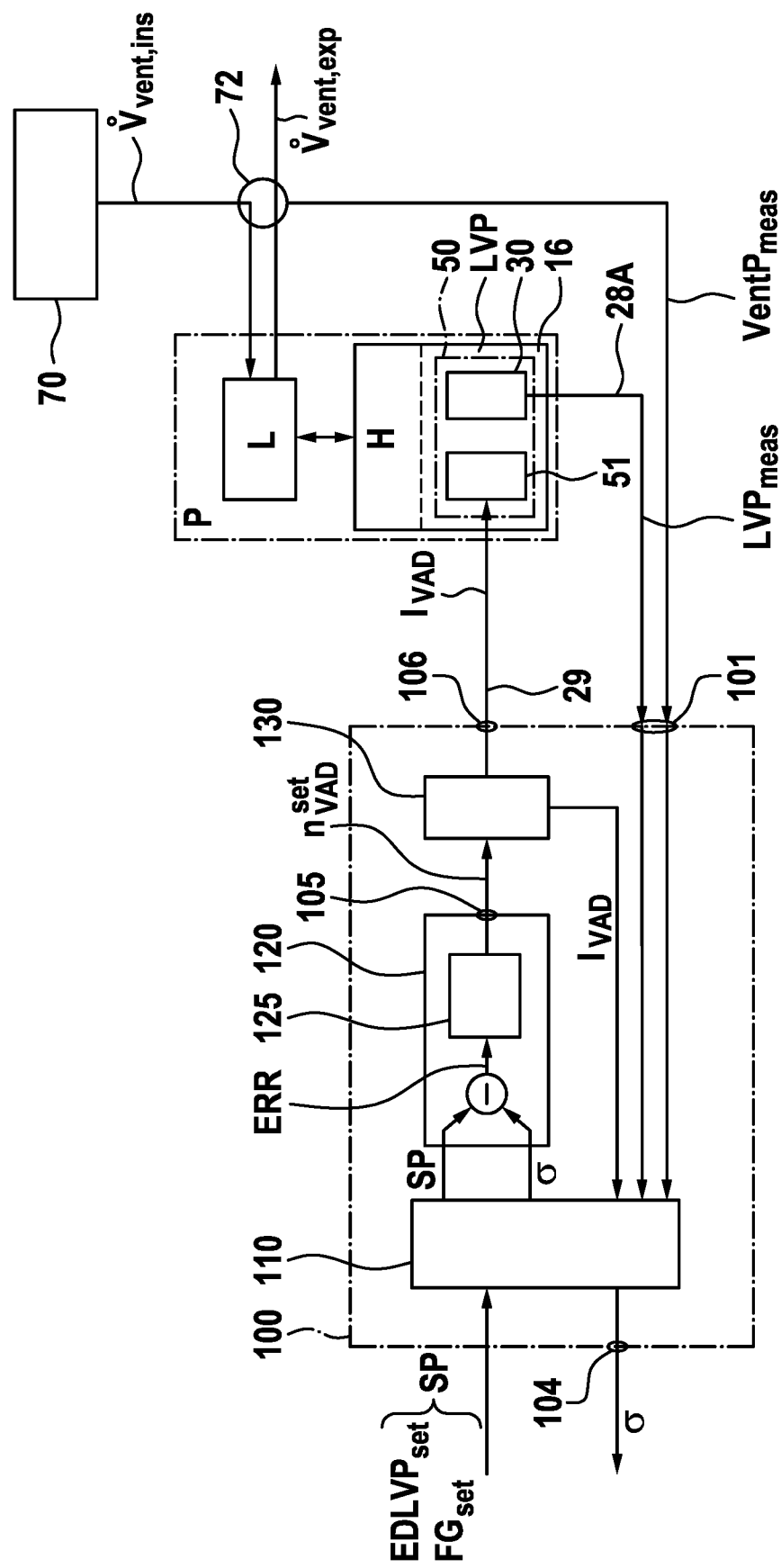
FIG. 3 shows the control device of FIG. 1 in an application context of a patient receiving heart assistance by the VAD and receiving breathing assistance by a lung ventilation device.

FIG. 3 shows an embodiment of an application of the improved control device 100 of FIG. 1 in the context of a patient P receiving heart assistance by the VAD 50 and breathing assistance by a lung ventilation device 70.

To start with, on the right-hand side of FIG. 3 a broken line box depicts the patient P. Further, box H depicts the heart of the patient P. For sake of simplicity, the lower half of the box H corresponds to the left ventricle 16 in which the flow cannula 53 with the inflow cage 54 of the pumping device 50 of FIGS. 1 and 2 as well as the sensor head 30 of one of the pressure sensors are located. The motor section 51, the pump section 52 and the pump housing 56 are located in the aorta after the aortic valve 15. The motor section 51 of the pumping device 50 produces the pumping speed of the pumping device 50. By supplying the necessary motor current $I_{VAD}$ via the power-supply line 29 by the motor control unit 130 of the control device 100 the speed of the VAD can be controlled based on the refined actual value EDLVP* or FG* as the at least one characteristic parameter σ.

Further shown in the box P is a box representing the lung L of the patient P. In the example, the patient P having an insufficient heart function receives heart assistance by the pumping device 50 and also ventilation assistance to the lung L by the ventilation device 70.

Due to the ventilation, the lung L is inflated and deflated. Thereby, the pressure in the thorax of the patient P is affected resulting in a synchronized variation of the intracardiac pressures. Thus, the measured left ventricular pressure LVP comprises corresponding physiologically caused fluctuations.

By means of a ventilation pressure sensor 72, the control device 100 receives a pressure signal sensed by the ventilation pressure sensor 72 being a measuring signal for the ventilation pressure $VentP_{meas}$.

The data processing unit 110 of the control device 100 is configured to perform continuously signal processing on the received measuring signal $LVP_{meas}$ to produce the refined actual value EDLVP* or FG* of the characteristic parameter ☐ in which physiologically caused fluctuations are eliminated or at least reduced. Additionally the data processing unit 110 is configured to perform continuously signal processing on the received measuring signal of the ventilation pressure $VentP_{meas}$.

For the control of the pump speed of the pumping device 50, the data processing unit 110 is configured to derive and process the actual values of the EDLVP detected in or derived from the corresponding measuring signal $LVP_{meas}$.

A refined actual value EDLVP* of the EDLVP or FG* as the characteristic parameter σ is forwarded to the speed command unit 120. The speed command unit 120 is configured to perform a comparison with the settable set-point value SP, such as $EDLVP_{set}$ or $FG_{set}$, for the EDLVP or FG and to generate a corresponding speed command signal $n_{VAD}^{set}$ supplied to the motor control unit 130, which, in turn, adjusts the motor current supplied to the electrical motor of the pumping device 50 accordingly.

Figure 5A:
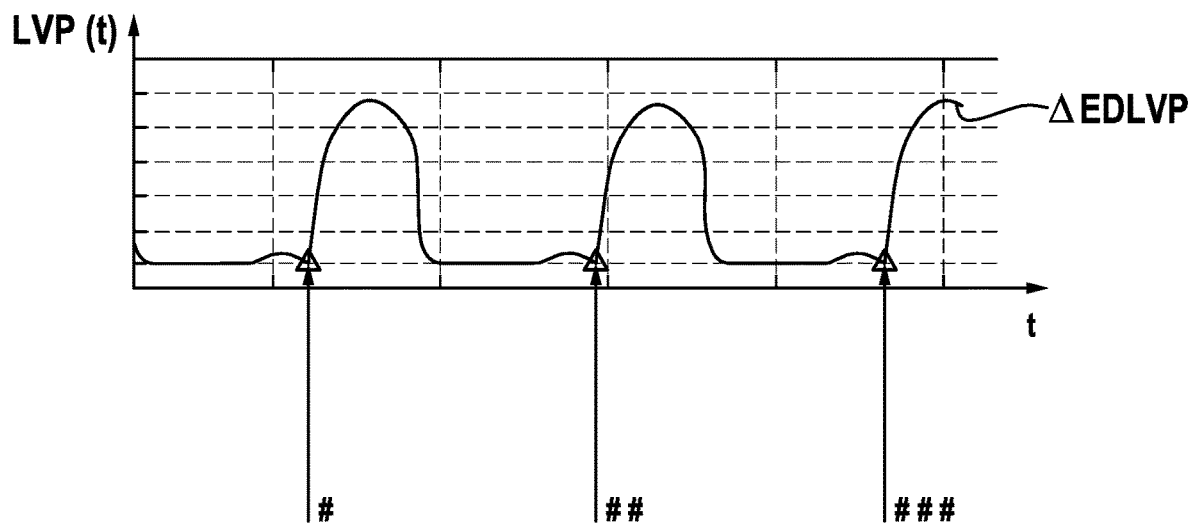
FIG. 5 illustrate the detection of end-diastolic pressure values in the left ventricular pressure signal.
Figure 5B:
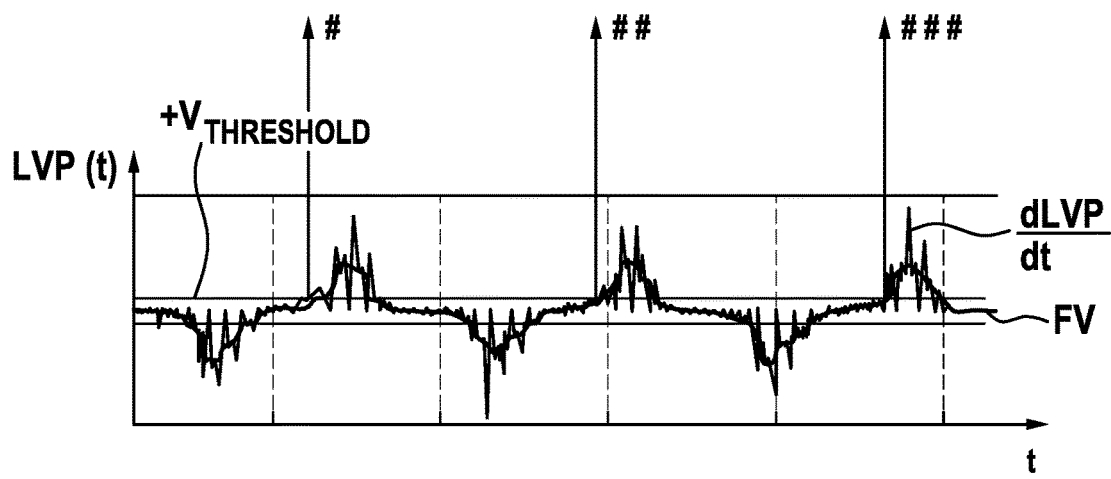

As illustrated in FIGS. 5A and 5B, to this end, the data processing unit 110 is configured to determine the actual value EDLVP based on a filtered (or smoothed) version FV of the first derivative $dLVP_{meas}/dt$ of the measuring signal $LVP_{meas}$ of the left-ventricular pressure.

For example, when it is determined that the first derivative $dLVP_{meas}/dt$ of the measuring signal $LVP_{meas}$ of the left ventricular pressure is equal a predetermined threshold value $v_{threshold}$ (and/or that further conditions are valid), the current actual value of the LVP is determined as the current actual value of the EDLVP.

Alternatively or additionally, the control device 100 may use the ECG signal provided by the ECG device 310. Here, the data processing unit 110 is configured to check as a further condition whether the ECG signal shows the R-wave. Further, with the ECG signal, the control device 100 can be configured to adjust the predetermined threshold value $v_{threshold}$ based on R-wave occurring in the ECG signal so that the actual value of the EDLVP can be determined based on the first derivative of $LVP_{meas}$ as discussed above.

In operation of the VAD, the control of the blood pump speed level is based on the refined actual value EDLVP* of the EDLVP and the corresponding set-point value SP. The speed command unit 120 is configured to calculate an error signal ERR based on the refined actual value EDLVP* and the set-point value SP. The speed command unit 120 is further configured to generate in the manner of a PID controller 125 based on the error signal ERR a correspondingly updated speed command signal $n_{VAD}^{set}$ supplied to the motor control unit 130.

The afore-discussed control principle for the speed level of the VAD based on the LVP as measuring signal representing a physical quantity related to the circulatory system can be modified to be based on any one or more other measuring signals representing physical quantities related to the circulatory system. For example, another or further vascular and/or intracardiac pressures, such as the aortic pressure AoP, the central venous pressure CVP and/or the pulmonary artery pressure PAP for right-sided heart assistance, and the ECG signal may be used.

As mentioned above, due to ventilation the lung L is inflated and deflated by ventilation device 70. Thereby, the pressure in the thorax of the patient P is affected resulting in a corresponding variation of the measuring signal $LVP_{meas}$. Consequently, during the inspiration phase, the derived EDLVP increases during the inspiration phases and decreases during the expiration phases. This causes corresponding physiologically caused fluctuations in the control of the speed level of the VAD.

Figure 4A:
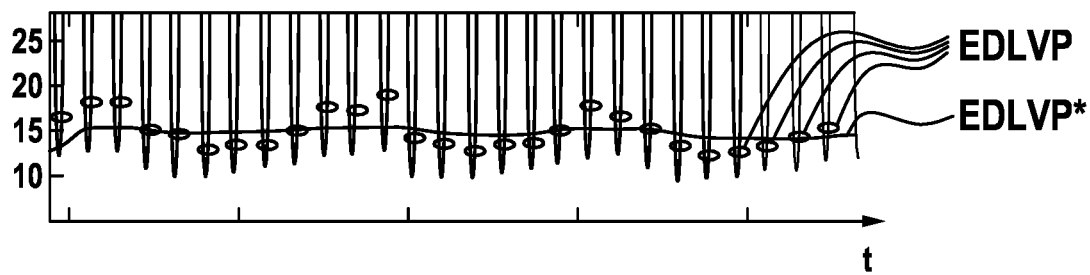
FIG. 4 illustrate physiologically caused fluctuations due to lung ventilation (FIG. 4C) on detected end-diastolic pressure values (FIG. 4A) and an end-diastolic pressure signal in which the physiologically caused fluctuations are reduced (FIG. 4A) and the rotational speed of the blood pump (FIG. 4B) under control of the control device.
Figure 4B:
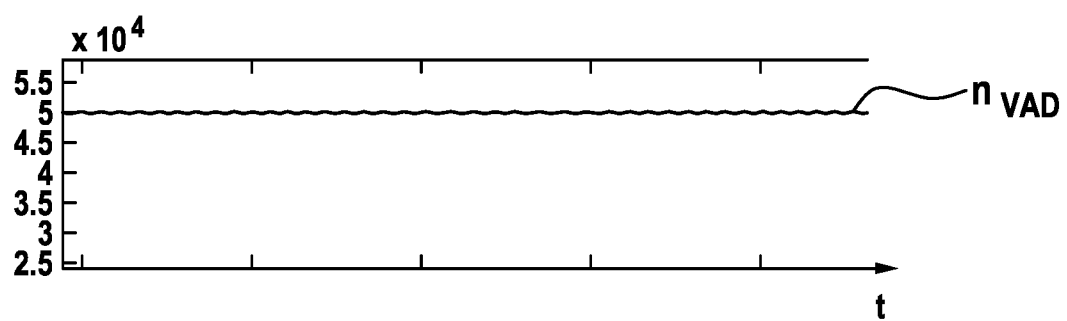
Figure 4C:
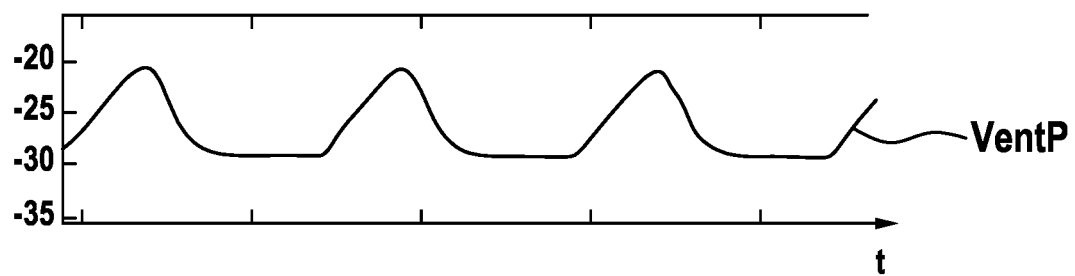

FIGS. 4A to 4C illustrate the ventilation induced variation of the derived actual values EDLVP. In FIG. 4A the measuring signal $LVP_{meas}$ (solid line) is drawn and the derived actual values EDLVP are marked by triangles. FIG. 4C shows the ventilation pressure VentP which causes corresponding fluctuations in the EDLVP values over time.

To eliminate these physiologically caused fluctuations, as a first approach, the data processing unit 110 is configured to apply an average filter on the derived actual values EDLVP.

Regarding the setup of the average filter, the data processing unit 110 may be configured to determine continuously, or every now and then, or periodically the ventilation frequency VF based on the measuring signal of the ventilation pressure $VentP_{meas}$.

It has been found that a filter size (or filter window) corresponding to the reciprocal value of the ventilation frequency VF, i.e. 1/VF, is effective to compensate for the effect of the ventilation. In other words, the data processing unit 110 can be configured to calculate for each point in time the actual mean value of the derived actual values EDLVP for a time interval related to the ventilation frequency VF.

For example, the time interval may be defined by the reciprocal value of the ventilation frequency VF or a multiple n thereof, i.e. $\frac{n}{VF}$ with n=1, 2, 3, . . . .

Alternatively, the data processing unit 110 can be configured to calculate the ventilation frequency VF by the time interval between two consecutive maxima or minima of the actual values EDLVP as discussed herein above.

Alternatively, instead of the moving average filter the applied filter may be a high-pass filer having a characteristic cut-off frequency set so that the physiologically caused fluctuations to be eliminated disappear. Particularly, the control device may be configured to set the characteristic cut-off frequency of the high-pass filter to the determined ventilation frequency VF.

As regards the speed level control of the VAD, the signal processing unit 110 of the control device 100, can be further or alternatively configured to determine the beginning and end of the heart contraction phases and the heart relaxation phases, respectively. The implemented value detection algorithm, which will be roughly explained in the following, is based on the measuring signals of the left ventricular pressure LVP and/or the aortic pressure AoP. Based on the determined begin and end of the respective heart contraction phase and heart relaxation phase, the contractility and heart relaxation can be calculated based thereon.

Figure 6A:
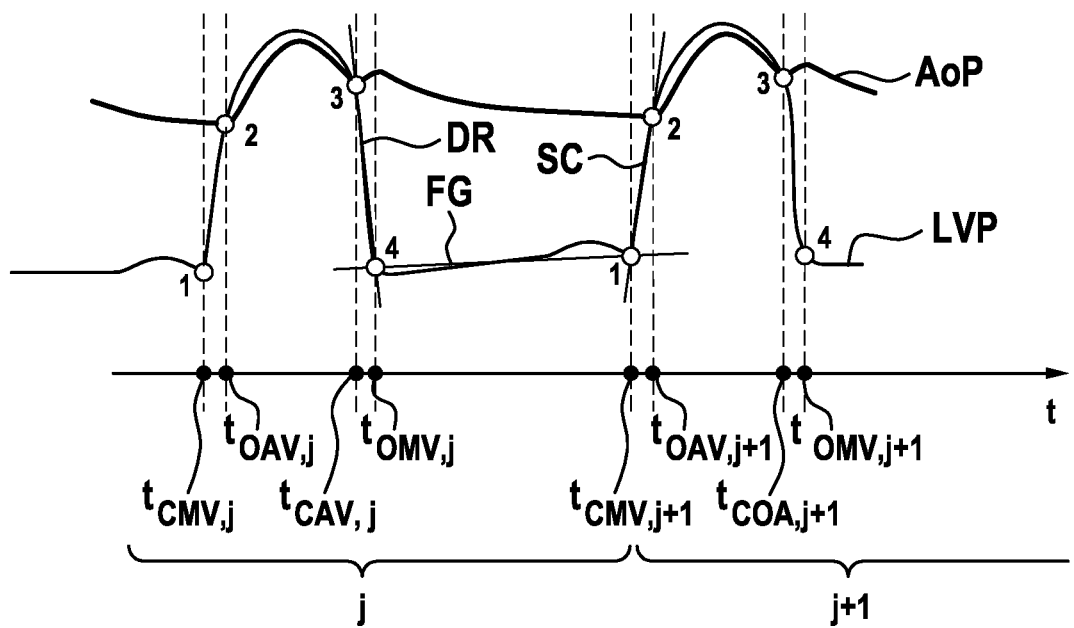
FIG. 6 show a diagram (FIG. 6A), of the left ventricular pressure signal during two cardiac cycles illustrating pressure gradients, such as the filling gradient (FIG. 6B), systolic contraction, and the diastolic relaxation, and particularly the filling gradient without VAD assistance (FIG. 6B), and the effect of a speed level control based on the filling gradient (FIG. 6C)

FIG. 6A shows a diagram of the pressure in the left ventricle LVP and in the aorta AoP during two cardiac cycles j, j+1 for illustration of the filling gradient FG, the systolic contraction SC, and the diastolic relaxation DR of the heart. These pressure gradients FG, SC, DR may also be (alternatively or additionally) used as a characteristic parameter in the control of the speed level of the VAD.

The term "cardiac cycle" used herein embraces the dynamic behavior of the heart during one heartbeat including e.g. the time-dependent changes of blood pressure and ventricular volume. The heartbeat herein is defined to start with the evocation of the atrial contraction, and to end right before the following atrial contraction, distinguishing between systole and diastole. The systole of the heart (also called the ejection phase of the heart) is the phase between the closing of the mitral valve and the closing of the aortic valve. The diastole (also called the filling phase of the heart) is the phase between the closing of the aortic valve and the closing of the mitral valve of the following heart cycle. The frequency of the heart passing through the cardiac cycle is known as the heart rate.

The respective points 1 to 4 in FIG. 6A mark respective particular characteristic events in each of the two shown cardiac cycles j, j+1, namely the closing of the mitral valve (point 1, CMV), the opening of the aortic valve (point 2, OAV), the closing of the aortic valve (point 3, COV), and the opening of the mitral valve (point 4, OMV). The following discussion is based on the cardiac cycle j.

Accordingly, the pressure gradient of the left ventricular pressure LVP during the systolic phase of the cardiac cycle between closing of the mitral valve (point 1) and opening of the aortic valve (point 2), which is defined as $$\left.\frac{\Delta LVP}{\Delta t}\right|_{SC} = \frac{LVP(t_{OAV,j}) - LVP(t_{CMV,j})}{t_{OAV,j} - t_{CMV,j}}$$

describes the systolic contraction SC, i.e. contractility of the heart, which may be used as a measure of cardiac pump performance, the degree to which muscle fibers can shorten when activated by a stimulus independent of preload and afterload; it is a major determinant of cardiac output and an important factor in cardiac compensation. The data processing unit 110 may be configured to calculate the actual systolic contraction SC as a characteristic parameter σ.

The pressure gradient of the left ventricular pressure LVP during the diastolic phase of the cardiac cycle between the closing of the aortic valve (point 3, COV) and the opening of the mitral valve (point 4, OMV), which is defined as $$\left.\frac{\Delta LVP}{\Delta t}\right|_{DR} = \frac{LVP(t_{OMV,j}) - LVP(t_{CAV,j})}{t_{OMV,j} - t_{CAV,j}}$$

describes the diastolic relaxation DR of the heart, which may be used to identify diastolic dysfunction, i.e. an abnormality in the relaxation phase of the heartbeat during which the heart is filling with blood in preparation for the next ejection. The data processing unit 110 may be configured to calculate the actual diastolic relaxation DR of the heart as a characteristic parameter σ.

Finally, the pressure gradient of the left ventricular pressure LVP during the diastolic phase of the cardiac cycle between the opening of the mitral valve (point 4, OMV) in the cardiac cycle j and the closing of the mitral valve (point 1, CMV) in the following cardiac cycle j+1, which is defined as $$\left.\frac{\Delta LVP}{\Delta t}\right|_{FG} = \frac{LVP(t_{CMV,j+1}) - LVP(t_{OMV,j})}{t_{CMV,j+1} - t_{OMV,j}}$$

is called filling gradient FG, which may be used as a measure describing whether the left ventricle does not properly relax and becomes stiff meaning the ventricle cannot fill with blood properly. The data processing unit 110 may be configured to calculate the actual filling gradient FG as a characteristic parameter σ.

Figure 6B:
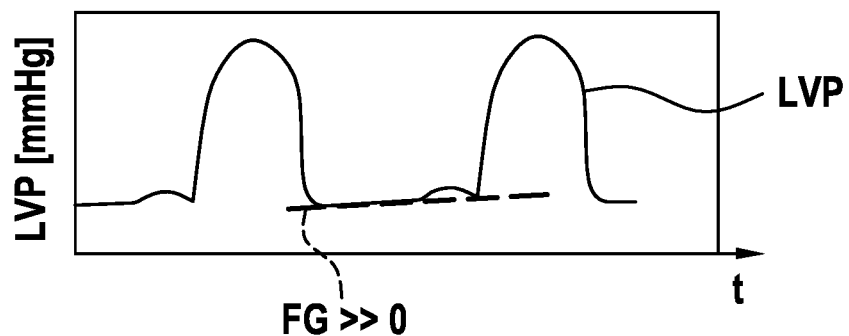
Figure 6C:
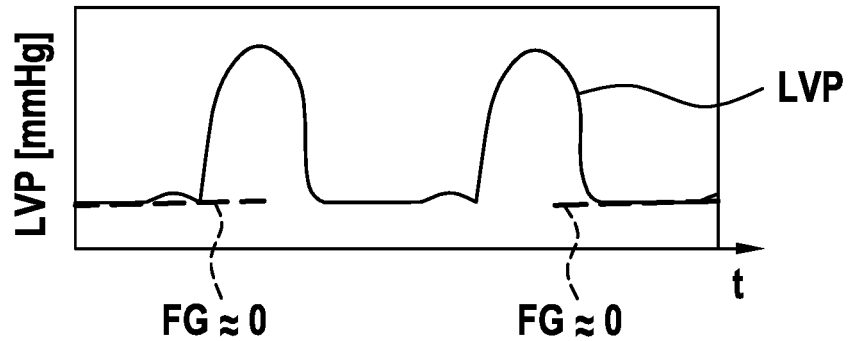

FIGS. 6B and 6C illustrate the effect of VAD speed control based on monitoring the filling gradient FG as the at least one characteristic parameter σ. To this end, the data processing unit 110 is configured to calculate the above discussed quotient of the difference of the left ventricular pressure value observed at the moment of opening of the mitral valve in an ending cardiac cycle j and at the moment of closing of the mitral valve in the consecutive following cardiac cycle j+1 divided by the time span therebetween.

FIG. 6B depicts the waveform of the LVP of an insufficient heart which is still loaded, i.e. not sufficiently assisted by application of a VAD. The left ventricle does not properly relax and becomes stiff so that the left ventricle cannot fill with blood properly. This is identified by thee filling gradient FG (dashed line in FIG. 6B) being positive and inclined, i.e. greater than zero.

FIG. 6C shows the effect of well-adjusted heart assistance by the VAD, in which the control of the VAD speed is based on monitoring of the filling gradient FG and the correspondingly adjusted speed of the VAD so that the amount of assistance provided by the VAD to the heart is such that the filling gradient becomes positive, but not negative to avoid suction. It is assumed that monitoring of the filling gradient FG and keeping it close to or equal to zero marks the suitable amount of heart assistance to unload the weakened heart and to support the heart in recovering.

Figure 7:
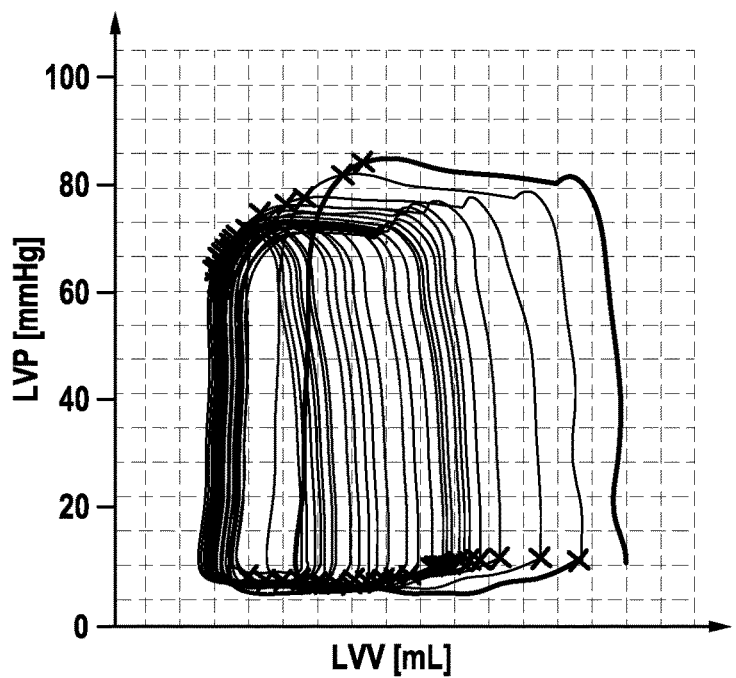
FIG. 7 further illustrates the effect of the VAD assistance of FIG. 6C by means of several pV-loops.

FIG. 7 further illustrates the effect of the heart assistance by the pumping device 50 based on the filling gradient FG (FIG. 6) as the at least one characteristic parameter σ on the variation of the left ventricular pressure LVP and the absolute left ventricular volume LVV during one cardiac cycle, which is called the characteristic pV-loop.

The effect on the shape and position of the pV-loop of the assisted heart is correlated with the amount of assistance provided by the VAD, such as the exemplary blood pump, which is correlated with the blood pump speed. It is noted, since blood flow produced by the pumping device of the VAD depends on the pressure difference between afterload and preload of the VAD, there is no linear relationship between the speed of the VAD and the produced blood flow and the provided assistance as well. But it is roughly correct to say that the amount of assistance may be increased by increasing the speed of the VAD.

The shown diagram of FIG. 7 starts in the situation of no support provided by the VAD (corresponding to FIG. 6B), which is reflected by the tall pV-loop (thick line) located in the middle and more to the right side of the diagram. With increasing support by the VAD, i.e. by the pumping device 50, the center of the pV-loop waveforms, connected to each other like a spiral, are shifted to the left side of the diagram, while the area of the respective pV-loop is becoming smaller and smaller. The area of the pV-look reflects the actual work produced by the heart itself, i.e. the actual load imposed on the heart. Thus, FIG. 7 illustrates the unloading of the heart by the pumping device 50. The clue is not the fact that the heart can be unloaded by assistance provided by the VAD. The clue is to find, maintain and adjust the actual amount of assistance so that the heart is just sufficiently unloaded to support the recovery thereof.

This can be done based on the herein-proposed speed level control using a suitable characteristic parameter σ such as the filling gradient FG discussed and illustrated in connection with FIG. 6.

For sake of completeness, it is known that the absolute volume of the left ventricle $V_{LV}$ may be monitored by means of an echocardiography device.

Figure 8:
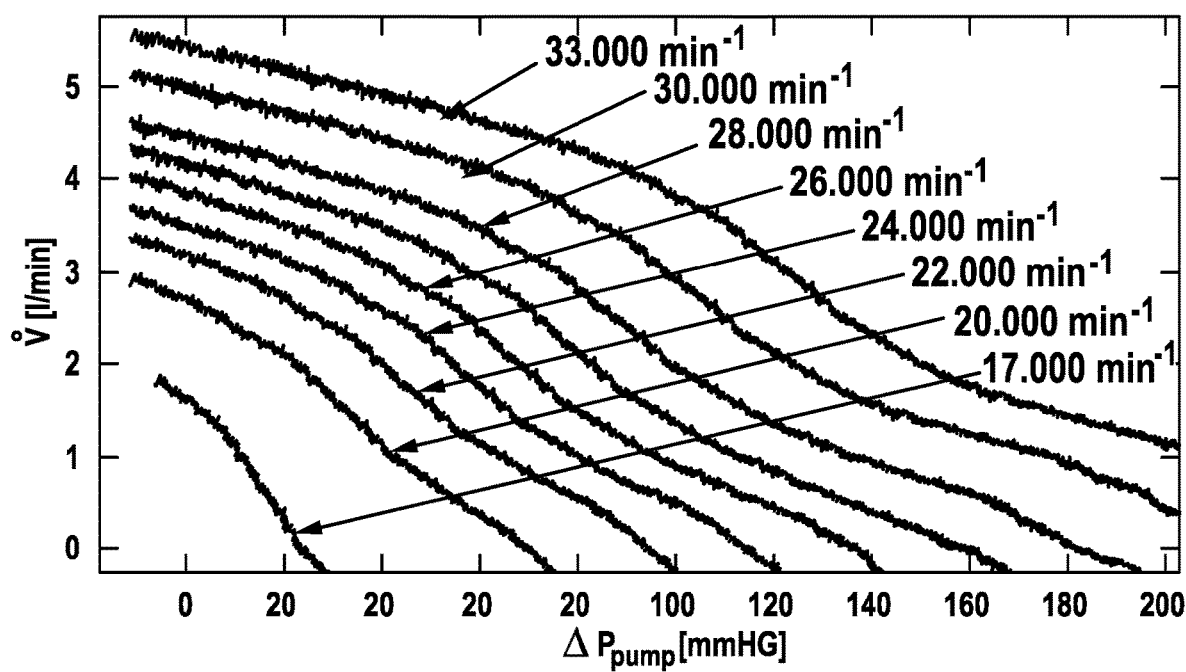
FIG. 8 is a diagram with characteristic curves indicating the relationship between an actual pressure difference $\Delta P_{pump}$ between preload and afterload at a rotary blood pump, an actual blood pump speed $n_{pump}$, and a corresponding blood flow produced by the blood pump $Q_{pump}$.

FIG. 8 is an exemplary diagram showing a set of characteristic curves representing the relationship between the actual pressure difference between the preload and the afterload of the blood pump $\Delta P_{pump}$, the actual blood pump speed $n_{pump}$, and the blood flow through the blood pump $Q_{pump}$ for the exemplary intravascular rotational blood pump as the herein used example of a VAD.

The actual blood flow $Q_{pump}$ through the blood pump can be determined as a function of the pressure difference $\Delta P_{pump}$ and the actual pump speed $n_{pump}$, $$Q_{pump} = f(\Delta P_{pump}, n_{pump}),$$

based on the set of characteristic curves. The actual pressure difference $\Delta P_{pump}$ can be determined by means of the pressure sensors 30, 60 in FIG. 2. The actual blood pump speed is known to the data processing unit 110, particularly in the speed command unit 120 and/or the motor control unit 130. Thus, the actual blood flow $Q_{pump}$ can be ascertained by the data processing unit 110. The relationship between the above-discussed values $\Delta P_{pump}$, $Q_{pump}$, and $n_{pump}$ described by the set of characteristic curves shown in FIG. 8 can be stored in a storage as a look-up table in the control device 100, e.g. a read only memory of the data processing unit 110 or in a storage on a chip in the blood pump or in the motor control unit 130.

FURTHER EMBODIMENTS

The present invention in particular concerns the following embodiments as defined in the following numbered items:
1. A control device (100) for a ventricular assist device, VAD (50), with settable speed levels, the control device (100) comprising an input (101) configured to receive at least one measuring signal ($LVP_{meas}$) related to a physiological condition of the circulatory system of a patient (P) receiving heart assistance by the VAD (50), wherein the control device (100) is configured to derive an actual value (EDLVP; FG) of at least one characteristic parameter of the heart (H) from one or more of the at least one measuring signal ($LVP_{meas}$) and to provide a refined actual value (EDLVP*; FG*) of the at least one characteristic parameter in which physiologically caused fluctuations are eliminated; and an output (105) configured to output an updated setting value ($n_{VAD}^{set}$) for the speed level, wherein the control device (100) is configured to produce the updated setting value ($n_{VAD}^{set}$) based on the refined actual value (EDLVP*; FG*) and a predeterminable set-point value ($EDLVP_{set}$; $FG_{set}$).
2. The control device (100) according to item 1, wherein the control device (100) is configured to process the one or more of the at least one measuring signal ($LVP_{meas}$) and/or a time series of actual values (EDLVP, FG) to provide the refined actual value (EDLVP*; FG*).
3. The control device (100) according to item 1 or 2, wherein the control device (100) is configured to process a plurality of actual values (EDLVP; FG) within a moving time interval that includes a current actual value (EDLVP; FG) and further historical actual values.
4. The control device (100) according to any one of the items 1-3, wherein the refined actual value (EDLVP*; FG*) is a moving average of a plurality of actual values (EDLVP; FG) and/or is based on a moving average of the one or more of the at least one measuring signal ($LVP_{meas}$).
5. The control device (100) according to any one of the items 1-4, wherein the control device (100) is configured to determine a breathing or ventilation frequency (VF) based on the at least one measuring signal ($LVP_{meas}$) and/or consecutive actual values (EDLVP; FG) and/or a measuring signal of a ventilation pressure.
6. The control device (100) according to any one of the items 1-5, wherein the control device (100) is configured
   to process the one or more of the at least one measuring signal ($LVP_{meas}$) or a sequence of actual values (EDLVP; FG) by applying a moving average filter having a size related to a periodicity of the physiologically caused fluctuations to be eliminated or to be reduced; and/or
   to process the one or more of the at least one measuring signal ($LVP_{meas}$) or the sequence of actual values (EDLVP; FG) by applying a high-pass filter having a characterizing cut-off frequency related to the physiologically caused fluctuations to be eliminated or to be reduced.
7. The control device (100) according to any one of the items 1-6, wherein at least one of the at least one measuring signal ($LVP_{meas}$) is at least one pressure in the circulatory system of the patient, namely at least one of a left ventricular pressure (LVP), an aortic pressure (AoP), a central venomous pressure (CVP), a pulmonary artery pressure (PAP), and/or an ECG signal of the patient.
8. The control device (100) according to any one of the items 1-7, wherein the at least one characteristic parameter is at least one of: a particular value of a vascular and/or an intracardiac pressure at a predetermined event of the cardiac cycle; a pressure gradient (SC, DR, FG) between two intracardiac pressures at two particular events during one cardiac cycle.
9. The control device (100) according to any one of the items 1-8, wherein the at least one characteristic parameter is a filling gradient $$\left.\frac{\Delta LVP}{\Delta t}\right|_{FG}$$

(FG) of the left ventricular pressure (LVP) during the diastolic phase of the cardiac cycle between the opening of the mitral valve (OMV) and closing of the mitral valve (CMV), which is defined as $$FG = \left.\frac{\Delta LVP}{\Delta t}\right|_{FG} = \frac{LVP(t_{CMV,j+1}) - LVP(t_{OMV,j})}{t_{CMV,j+1} - t_{OMV,j}}$$

and wherein the control device (100) is configured to produce the updated setting values ($n_{VAD}^{set}$) so that the filling gradient $$\left.\frac{\Delta LVP}{\Delta t}\right|_{FG}$$

becomes or is kept positive and close to zero, preferably zero.

10. The control device (100) according to any one of the items 1-9, wherein control device (100) is further configured
   to calculate an actual heart rate based on the time interval between an occurrence and a consecutive recurrence of one of the at least one characteristic parameter (EDLVP; FG) and/or
   to calculate an actual blood flow produced by the VAD (50).

11. The control device (100) according to any one of the items 1-10,
   wherein control device (100) is configured to produce an updated setting value ($n_{VAD}^{set}$) each time there is a predetermined difference between the refined actual value (EDLVP*; FG*) and the corresponding set-point value (EDLVP$_{set}$; FG$_{set}$); and/or
   wherein control device (100) is configured to update the setting value ($n_{VAD}^{set}$) when a new refined actual value (EDLVP*, FG*) has been produced; and/or
   wherein control device (100) is configured to update the setting value ($n_{VAD}^{set}$) periodically with a predetermined frequency.

12. The control device (100) according to any one of the items 1-10, wherein control device (100) is configured to display the refined actual value (EDLVP*; FG*) on a display (210) and/or to provide the refined actual value (EDLVP*) at an output (104) of the control device (100).

13. A VAD (50) for assistance of a heart, comprising the control device (100) of any one of items 1 to 12,
   wherein the VAD (50) is preferably a non-pulsatile rotational blood pump;
   wherein further preferably the blood pump is catheter-based; and
   wherein most preferably the VAD (50) is a low-inertia device by featuring one or more of the following: moving, in particular rotating, parts, for example a rotor or impeller, of the VAD comprise low masses by being made of a low-weight material, for example plastic; a driving means, such as an electric motor, is arranged near, preferably very near, most preferably adjacent, to a part, for example a rotor or impeller, driven by the motor, and, if catheter-based, preferably having no rotational drive cable; a coupling or connection, for example a shaft, of the motor with a part, for example a rotor or impeller, driven by the motor is short; all moving, in particular rotating, parts of the VAD have small diameters.

14. A method for obtaining a refined actual value of at least one characteristic parameter of the heart (H), the method comprising
   receiving at least one measuring signal (LVP$_{meas}$) related to a physiological condition of the circulatory system of a patient (P);
   deriving an actual value (EDLVP; FG) of at least one characteristic parameter of the heart (H) from one or more of the at least one measuring signal (LVP$_{meas}$);
   processing the actual value (EDLVP; FG) or one or more of the at least one measuring signal (LVP$_{meas}$) to provide the refined actual value (EDLVP*; FG*) in which physiologically caused fluctuations are eliminated or reduced.

15. A method for controlling the speed level of a ventricular assist device, VAD (50), with settable speed levels, the method comprising
   obtaining a refined actual value of at least one characteristic parameter of the heart (H) by the method according to item 14; and
   producing an updated setting value ($n_{VAD}^{set}$) for the speed level based on the refined actual value (EDLVP*; FG*) and a predeterminable set-point value (EDLVP$_{set}$; FG$_{set}$).

16. The method of item 14, further comprising processing the one or more of the at least one measuring signal (LVP$_{meas}$) or a time series of the actual values (EDLVP, FG) to provide the refined actual value (EDLVP*; FG*).

17. The method of item 14 or 15, further comprising processing a plurality of actual values (EDLVP; FG) within a moving time interval that includes a current actual value (EDLVP; FG) and further historical actual values.

18. The method of any one of the items 14-17, further comprising determining a breathing or ventilation frequency (VF) of the patient (P) based on the at least one measuring signal (LVP$_{meas}$) and/or consecutive actual values (EDLVP; FG) and/or a measuring signal of a ventilation pressure.

19. The method of any one of the items 14-18, further comprising
   processing the one or more of the at least one measuring signal (LVP$_{meas}$) or a sequence of actual values (EDLVP; FG) by applying a moving average filter having a size related to a periodicity of the physiologically caused fluctuations to be eliminated or to be educed; and/or
   processing the one or more of the at least one measuring signal (LVP$_{meas}$) or the sequence of actual values (EDLVP; FG) by applying a high-pass filter having a characterizing cut-off frequency related to the physiologically caused fluctuations to be eliminated or to be reduced.

20. The method of any one of the items 14-19, wherein at least one of the at least one measuring signal (LVP$_{meas}$) is at least one pressure in the circulatory system of the patient, namely at least one of a left ventricular pressure (LVP), an aortic pressure (AoP), a central venomous pressure (CVP), a pulmonary artery pressure (PAP), and/or an ECG signal of the patient.

21. The method of any one of the items 14-20, wherein the at least one characteristic parameter is at least one of: a particular value of a vascular and/or intracardiac pressure at a predetermined event of the cardiac cycle; a pressure gradient between two intracardiac pressures at two particular events during one cardiac cycle.

22. The method of any one of the items 14-21, wherein the at least one characteristic parameter is a filling gradient $$\left.\frac{\Delta LVP}{\Delta t}\right|_{FG}$$

(FG) of the left ventricular pressure (LVP) during the diastolic phase of the cardiac cycle between the opening of the mitral valve (OMV) and closing of the mitral valve (CMV), which is defined as $$FG = \left.\frac{\Delta LVP}{\Delta t}\right|_{FG} = \frac{LVP(t_{CMV,j+1}) - LVP(t_{OMV,j})}{t_{CMV,j+1} - t_{OMV,j}}$$

and wherein the control device (100) is configured to produce the updated setting values ($n_{VAD}^{set}$) so that the filling gradient $$\left.\frac{\Delta LVP}{\Delta t}\right|_{FG}$$

(FG) becomes or is kept positive and close to zero, preferably zero.

23. The method of any one of the items 14-21, further comprising calculating an actual heart rate based on the time interval between an occurrence and a consecutive recurrence of one of the at least one actual value (EDLVP; FG) and/or calculating an actual blood flow produced by the VAD (50).

24. The method of any one of the items 14-23, further comprising
updating the setting value ($n_{VAD}^{set}$) each time there is a predetermined difference between the refined actual value (EDLVP*; FG*) and the corresponding set-point value (EDLVP$_{set}$; FG$_{set}$); and/or
updating the setting value ($n_{VAD}^{set}$) when a new refined actual value (EDLVP*; FG*) has been produced; and/or
updating the setting value ($n_{VAD}^{set}$) periodically with a predetermined frequency.

25. The control device (100) according to any one of the items 1-12 or the method according to any one of the items 14-24, wherein the physiologically caused fluctuations to be eliminated or to be reduced are correlated with at least one of pressure fluctuations in the thorax of the patient (P), pressure fluctuations caused by autonomous or assisted breathing of the patient (P), pressure fluctuations caused by an intra-aortic balloon pump in the aorta of the patient, pressure fluctuations caused by an external counter-pulsation therapy applied to the patient, pressure fluctuations caused by a change of the patient's positioning, for example into such as the Trendelenburg position.

The invention claimed is:
1. A control device for a ventricular assist device (VAD) with settable speed levels, the control device comprising:
an input configured to receive at least one measuring signal related to a physiological condition of the circulatory system of a patient receiving heart assistance by the VAD, wherein the control device is configured to derive an actual value of at least one characteristic parameter of the heart from the at least one measuring signal and to provide a refined actual value of the at least one characteristic parameter in which effects of physiologically caused fluctuations are eliminated or reduced; and
an output configured to output an updated setting value for the speed level, wherein the control device is configured to produce the updated setting value based on the refined actual value and a predeterminable set-point value,
wherein the at least one characteristic parameter is a filling gradient of the left ventricular pressure during the diastolic phase of a cardiac cycle between the opening of the mitral valve and the closing of the mitral valve, and wherein the control device is configured to produce the updated setting values so that the filling gradient becomes or is kept positive and close to zero.

2. The control device according to claim 1, wherein the control device is configured to process at least one of the at least one measuring signal or the actual value to provide the refined actual value.

3. The control device according to claim 1, wherein the control device is configured to process a plurality of actual values within a moving time interval that includes a current actual value and historical actual values.

4. The control device according to claim 1, wherein the refined actual value is a moving average of a plurality of actual values or is based on a moving average of the at least one measuring signal.

5. The control device according to claim 1, wherein the control device is configured to determine a breathing or ventilation frequency based on the at least one measuring signal, historical actual values, or a measuring signal of a ventilation pressure.

6. The control device according to claim 1, wherein the control device is configured to:
process the at least one measuring signal or a sequence of actual values by applying a moving average filter having a size related to a periodicity of the physiologically caused fluctuations to be eliminated; or
process the at least one measuring signal or the sequence of actual values by applying a high-pass filter having a characterizing cut-off frequency related to the physiologically caused fluctuations to be eliminated.

7. The control device according to claim 1, wherein the at least one measuring signal includes at least one pressure in the circulatory system of the patient.

8. The control device according to claim 1, wherein the control device is further configured to:
calculate an actual heart rate based on the time interval between an occurrence and a consecutive recurrence of one of the at least one characteristic parameter; or
calculate an actual blood flow produced by the VAD.

9. The control device according to claim 1, wherein the control device is configured to:
update the setting value each time there is a predetermined difference between a refined actual value and a corresponding set-point value;
update the setting value when a new refined actual value has been produced; or
update the setting value periodically with a predetermined frequency.

10. The control device according to claim 1, wherein control device is further configured to:
display the refined actual value on a display; or
provide the refined actual value at an output.

11. The control device according to claim 1, wherein the physiologically caused fluctuations to be eliminated or to be reduced are correlated with pressure fluctuations caused by autonomous or assisted breathing of the patient, pressure fluctuations caused by an intra-aortic balloon pump in the aorta of the patient, pressure fluctuations caused by an external counter-pulsation therapy applied to the patient, or pressure fluctuations caused by a change of the patient's positioning.

12. A system for assistance of a heart, the system comprising:
   a ventricular assist device (VAD) with settable speed levels, wherein the VAD comprises a rotor and an electric motor having a shaft, and wherein the shaft is coupled to the rotor and configured to drive the rotor; and
   a control device configured to:
      receive at least one measuring signal related to a physiological condition of the circulatory system of a patient receiving heart assistance by the VAD;
      derive an actual value of at least one characteristic parameter of the heart from the at least one measuring signal;
      process the actual value or the at least one measuring signal to derive a refined actual value in which physiologically caused fluctuations are eliminated or reduced; and
      update a setting value for a speed level of the VAD based on the refined actual value and a predeterminable set-point value.

13. The system according to claim 12, wherein the at least one characteristic parameter is a pressure gradient between two intracardiac pressures at two particular events during one cardiac cycle.

14. The system according to claim 13, wherein the pressure gradient is a filling gradient, a systolic contraction, or a diastolic relaxation of the heart.

15. The system according to claim 12, wherein the controller is configured to update the setting value for the speed level of the VAD to unload a weakened heart of the patient.

16. The system according to claim 15, wherein the at least one measuring signal represents a left ventricular pressure as at least one physical value.

17. The system according to claim 16, wherein the VAD further comprises a sensor configured to generate the at least one measuring signal.

18. The system according to claim 17, wherein the sensor is configured to be positioned in a left ventricle of the patient.

19. The system according to claim 18, wherein the VAD is configured to extend across an aortic valve of the patient.

20. A method for assistance of a heart, the method comprising
   receiving, with one or more processors, at least one measuring signal related to a physiological condition of the circulatory system of a patient receiving heart assistance by a ventricular assist device (VAD) with settable speed levels, wherein the VAD comprises a rotor and an electric motor having a shaft, and wherein the shaft is coupled to the rotor and configured to drive the rotor;
   deriving, with the one or more processors, an actual value of at least one characteristic parameter of the heart from the at least one measuring signal;
   processing, with the one or more processors, the actual value or the at least one measuring signal to provide a refined actual value in which physiologically caused fluctuations are eliminated or reduced; and
   updating, with the one or more processors, a setting value for a speed level of the VAD based on the refined actual value and a predeterminable set-point value.

* * * * *